United States Patent
Rana et al.

(10) Patent No.: US 10,342,850 B2
(45) Date of Patent: *Jul. 9, 2019

(54) OCTREOTIDE INJECTION

(71) Applicant: SUN PHARMACEUTICAL INDUSTRIES LIMITED, Mumbai, Maharashtra (IN)

(72) Inventors: Amar Rana, Baroda (IN); Rakesh Thummar, Baroda (IN); Sudeep Agrawal, Baroda (IN); Subhas Balaram Bhowmick, Baroda (IN); Rajamannar Thennati, Baroda (IN)

(73) Assignee: SUN PHARMACEUTICAL INDUSTRIES LIMITED, Mumbai (IN)

(*) Notice: Subject to any disclaimer, the term of this patent is extended or adjusted under 35 U.S.C. 154(b) by 0 days.

This patent is subject to a terminal disclaimer.

(21) Appl. No.: 16/124,781

(22) Filed: Sep. 7, 2018

(65) Prior Publication Data

US 2019/0000918 A1    Jan. 3, 2019

Related U.S. Application Data

(63) Continuation of application No. 15/980,287, filed on May 15, 2018, now abandoned.

(30) Foreign Application Priority Data

May 15, 2017    (IN) .............. 201721017024

(51) Int. Cl.
| | | |
|---|---|---|
| A61K 47/26 | (2006.01) | |
| A61K 47/14 | (2017.01) | |
| A61K 47/12 | (2006.01) | |
| A61K 38/12 | (2006.01) | |
| A61K 9/08 | (2006.01) | |
| A61K 9/00 | (2006.01) | |
| A61K 47/10 | (2017.01) | |
| A61K 38/08 | (2019.01) | |

(52) U.S. Cl.
CPC ............ *A61K 38/12* (2013.01); *A61K 9/0019* (2013.01); *A61K 9/08* (2013.01); *A61K 38/08* (2013.01); *A61K 47/10* (2013.01); *A61K 47/12* (2013.01); *A61K 47/14* (2013.01); *A61K 47/26* (2013.01)

(58) Field of Classification Search
CPC ...... A61K 38/08; A61K 38/31; A61K 9/0019; A61M 5/31533
See application file for complete search history.

(56) References Cited

U.S. PATENT DOCUMENTS

| | | |
|---|---|---|
| 5,538,739 A | 7/1996 | Bodmer et al. |
| 2010/0203014 A1 | 8/2010 | Maggio |
| 2014/0213984 A1 | 7/2014 | Pawar et al. |

FOREIGN PATENT DOCUMENTS

| | | |
|---|---|---|
| AT | 402 896 B | 9/1997 |
| CA | 2 473 412 A1 | 1/2006 |
| EP | 2 662 073 A1 | 11/2013 |
| WO | 2011/076368 A2 | 6/2011 |

OTHER PUBLICATIONS

Jan Jezek, Biopharmaceutical formulations for pre-filled delivery devices, ISSN: 1742-5247 (Print) 1744-7593 (Online), 2013.*
PCT/ISA/220, Dated Oct. 31, 2018.

* cited by examiner

*Primary Examiner* — James H Alstrum-Acevedo
*Assistant Examiner* — Erinne R Dabkowski
(74) *Attorney, Agent, or Firm* — Sughrue Mion, PLLC (57) ABSTRACT

The present invention relates to a sterile solution comprising: octreotide in the form of a pharmaceutically acceptable salt, present at a concentration equivalent to 2.0 mg/ml to 2.5 mg/ml of octreotide base, and at least one preservative in a pharmaceutically acceptable vehicle, wherein the sterile solution is present in an injection device.

8 Claims, 2 Drawing Sheets

OCTREOTIDE INJECTION

FIELD OF INVENTION

The present invention relates to a sterile solution of octreotide in the form of a pharmaceutically acceptable salt filled in an injection device, wherein the octreotide salt is present at a concentration equivalent to 2.0 mg/ml to 2.5 mg/ml of octreotide base.

BACKGROUND OF INVENTION

Octreotide is commercially available under the brand name Sandostatin™ as a preserved solution filled in sterile 5 ml multidose vials in two strengths, 200 μg/ml and 1000 μg/ml. The present inventors had previously developed a multiple dose pen injection device containing solution of octreotide acetate that allowed self-administration of octreotide dose to the patients, as disclosed in the US Pat. Appl. Publ. No. 20140213984A1. During this time, the present inventors worked towards the development of an injection device, such as a pen injection device, having multiple doses that supply daily doses of octreotide for about a month or so. In particular, attempts were made to develop a solution of octreotide that had 5 times higher concentration, i.e. 5 mg/ml compared to the vial product Sandostatin™, so that the volume of injection is reduced five times. Advantageously, since the concentration of octreotide was increased five times, the volume required to deliver equivalent dose was lowered five times, and correspondingly, the amount of preservative injected was reduced five times.

Typically it is known that peptide drugs, after oral or parenteral administration, show a poor bioavailability in the blood, e.g. due to their short biological half-lives in turn caused by their metabolic instability (see the disclosure in U.S. Pat. No. 5,538,739). The present inventors have faced the same problem of poor bioavailability for octreotide, as disclosed in the prior art.

An aqueous solution of octreotide acetate at a concentration equivalent to 5 mg/ml of octreotide base (as disclosed in example 1 of US 20140213984A1) filled in a pen injection device was injected subcutaneously in 20 microliters volume to human volunteers. The relative bioavailability of the octreotide acetate was determined and was compared with a Sandostatin™ solution that has 1 mg/ml octreotide acetate concentration, prepared in a volume of 100 microliters and injected through a conventional syringe. Surprisingly, the test sample of octreotide acetate provided only a 5% relative bioavailability, as compared to the Sandostatin™ solution.

Thus, it is an object of the present invention to solve the technical problem of poor bioavailability of octreotide in a salt form.

The present inventors have discovered a specific concentration range of 2.0 to 2.5 mg of octreotide base per ml of the solution, which unexpectedly provided satisfactory bioavailability equivalent to the Sandostatin™ 1 mg/ml solution at the same dosage.

SUMMARY OF THE INVENTION

The present invention provides a sterile solution comprising octreotide in the form of its salt present at a concentration equivalent to 2.0 mg/ml to 2.5 mg/ml of octreotide base and at least one preservative in a pharmaceutically acceptable vehicle, wherein the solution is present in an injection device.

DETAILED DESCRIPTION OF THE INVENTION

As used herein, the term "bioavailability" generally means the rate and extent to which the active ingredient, i.e. octreotide is absorbed from the site of injection and becomes available in parenteral circulation.

This invention discloses the following unexpected findings: (1) sub-cutaneous administration of a solution of octreotide base in the form of its salt, having a concentration of 5.0 mg/ml when administered subcutaneously at a dosage of 100 micrograms in an injection volume of 20 microliters via a pen injection device, provided a bioavailability that was significantly lower than the bioavailability provided by sub-cutaneous administration of same dose of control solution (Sandostatin™ 1 mg/ml octreotide solution) administered via a conventional syringe), and (2) in a similar study, when a solution of octreotide base in the form of its salt having a concentration of 2.5 mg/ml was administered subcutaneously at a dose of 100 micrograms in an injection volume of 40 microliters via a pen injection device, the bioavailability observed was unexpectedly equivalent to the bioavailability provided by administration of same dose of control solution (Sandostatin™ 1 mg/ml octreotide solution), administered in an injection volume of 100 microliters through the conventional syringe.

The present invention thus provides a sterile solution comprising: octreotide, in the form of a pharmaceutically acceptable salt, present at a concentration equivalent to 2.0 mg/ml to 2.5 mg/ml of octreotide base, and at least one preservative in a pharmaceutically acceptable vehicle, wherein the sterile solution is present in an injection device. This sterile solution comprising an octreotide salt form, when administered subcutaneously through the injection device to human, provides a bioavailability equivalent to that obtained by administration of same dose of octreotide via injection of marketed Sandostatin™ 1 mg/ml solution through a conventional needle syringe injection system.

In some preferred embodiments, the salt of octreotide include pharmaceutically acceptable salts, such as acid addition salts. Acid addition salts may be formed by inorganic acid, organic acid or polymeric acid, for eg. hydrochloric acid, acetic acid, lactic acid, citric acid, fumaric acid, malonic acid, maleic acid, tartaric acid, aspartic acid, benzoic acid, succinic acid or pamoic acid. This includes simple salt forms of octreotide e.g., octreotide acetate, octreotide lactate and octreotide maleate; less water soluble octreotide salt forms e.g., octreotide pamoate and fatty acid octreotide salt forms e.g., octreotide palmitate and octreotide stearate. In accordance with the embodiments, the acid addition salts may exist as monovalent or divalent salts, depending upon whether 1 or 2 acid equivalents are added. In one preferred embodiment, the salt of octreotide is octreotide acetate.

According to the present invention, the sterile solution comprises octreotide in the form of a pharmaceutically acceptable salt, present at a concentration equivalent to 2.0 mg/ml to 2.5 mg/ml octreotide base, for example, 2.005, 2.006, 2.007, 2.008, 2.009, 2.01, 2.02, 2.03, 2.04, 2.05, 2.06, 2.07, 2.08, 2.09, 2.1, 2.15, 2.2, 2.25, 2.3, 2.35, 2.4, 2.45 or 2.50 mg/ml of octreotide base. In one embodiment, the sterile solution comprises octreotide in the form of a salt at a concentration in the range of 2.01 to 2.50 mg per ml of octreotide base. In another embodiment, the sterile solution comprises octreotide in the form of its salt at a concentration in the range of 2.1 to 2.5 mg per ml octreotide base. In one particularly preferred embodiment, the sterile solution comprises octreotide in the form of a salt at a concentration equivalent to 2.5 mg per ml octreotide base.

In one preferred embodiment, the present invention provides a sterile solution comprising octreotide acetate present at a concentration equivalent to 2.0 mg/ml to 2.5 mg/ml of octreotide base and at least one preservative in a pharmaceutically acceptable vehicle, wherein the solution is present in a an injection device, such as a pen injection device.

Preferably, the injection device is a multiple dose pen injection device, comprising: a cartridge holding the sterile solution of octreotide, as a reservoir, in volume ranges selected from: 1.0 ml to 10.0 ml, preferably 2.0 ml to 5.0 ml, more preferably 2.5 ml to 3.5 ml and 2.8 ml to 3.2 ml; specific volumes selected from such as for example 2.5, 2.6, 2.7, 2.8, 2.9, 3.0, 3.1, 3.2, 3.3, 3.4 or 3.5 ml. In one preferred embodiment, the volume of solution contained in the injection device is in the range of 2.8 ml to 3.2 ml.

A portion of the sterile solution from the injection device is injected to deliver a particular dose to the patient, and the total solution contained in the injection device is suitable to deliver multiple daily doses over consecutive days for the period of therapy.

In preferred embodiments, the injection device is configured to inject 20 to 250 microliters of the solution in order to provide octreotide in an amount in the range from 40 µg to 625 µg per injection. In one or more embodiments, the injection device is configured to inject per administration, a volume in the range of about 20 µL to 250 µL, such as for example 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, 125 µL, 150 µL, 175 µL, 200 µL or 225 µL, preferably from about 20 µL to about 80 µL. In preferred embodiments, the present invention provides 20 to 80 microliters of the sterile solution per injection such as for example 20, 40, 60 or 80 microliters to deliver a dosage of octreotide in the range of 50 µg to 200 µg per injection, such as for example 50, 100, 150 or 200 µg per injection.

In one preferred embodiment, the present invention provides a sterile solution comprising octreotide acetate present at a concentration equivalent to 2.0 to 2.5 mg/ml of octreotide base and at least one preservative in a pharmaceutically acceptable vehicle, wherein the solution is present in an injection device in volumes ranging from 2.0 ml to 5.0 ml, and further wherein the injection device is configured to inject 20 to 250 microliters of the solution per injection to a patient in order to provide octreotide in an amount in the range from 40 µg to 625 µg per injection.

In particularly preferred embodiment, the present invention provides a sterile solution comprising octreotide acetate present at a concentration equivalent to 2.5 mg/ml of octreotide base and at least one preservative in a pharmaceutically acceptable vehicle, wherein the solution is present in an injection device in volumes ranging from 2.0 ml to 3.0 ml, and further wherein the injection device is configured to inject 20 to 80 microliters of the solution per injection to a patient in order to provide octreotide in an amount in the range from 50 µg to 200 µg per injection.

In one particularly preferred embodiment, the present invention provides a sterile solution comprising octreotide acetate present at a concentration equivalent to 2.5 mg/ml of octreotide base and at least one preservative in a pharmaceutically acceptable vehicle, wherein the solution is present in a pen injection device, and further wherein administration of 40 µl of the solution through the pen injection device delivers a dosage equivalent to 100 µg of octreotide base per injection.

In another preferred embodiment, the present invention provides a sterile solution comprising octreotide acetate present at a concentration equivalent to 2.5 mg/ml of octreotide base and at least one preservative in a pharmaceutically acceptable vehicle, wherein the solution is present in a pen injection device, and further wherein administration of 80 µl of the solution through the pen injection device delivers a pen injection device dosage equivalent to 200 µg of octreotide base per injection.

In other embodiment, the present invention provides a sterile solution comprising octreotide acetate present at a concentration equivalent to 2.5 mg/ml of octreotide base and at least one preservative in a pharmaceutically acceptable vehicle, wherein the solution is present in a pen injection device, and further wherein administration of 60 µl of the solution through the pen injection device delivers a dosage equivalent to 150 µg of octreotide base per injection.

In preferred embodiments, desired volume of the sterile solution based on desired dose can be accurately administered using a specific dose dialing facility present in the injection device. The injection device can have appropriate unit µg markings in the dose dial window varying from 40 to 625, such as for example 40, 50, 75, 100, 125, 150, 175, 200, 225, 250, 275, 300, 325, 350, 375, 400, 425, 450, 475, 500, 525, 550, 575, 600, 625, 650 or 675, preferably 50 to 200, indicating unit dosage in µg administered when dialed to that specific marking.

In one or more embodiments, a different dosage of octreotide may be administered using varied volume of the aqueous solution of octreotide acetate, such as for example, a 100 µg dosage can be administered by injecting 50 µL sterile solution having 2.0 mg/ml octreotide base or alternatively by injecting a 40 µL of solution having 2.5 mg/ml octreotide base or alternatively by injecting a 45.5 µL of solution having 2.2 mg/ml octreotide base. Similarly, a 200 µg dose can be administered by injecting a 100 µL sterile solution having 2.0 mg/ml octreotide base or alternatively by injecting an 80 µL of solution having 2.5 mg/ml octreotide base or alternatively by injecting 91 µL of solution having 2.2 mg/ml octreotide base.

In one particularly preferred embodiment, the sterile solution of octreotide or its pharmaceutically acceptable salt comprises:

| Ingredients | Concentration in mg/ml |
| --- | --- |
| Octreotide base in the form of its salt | 2.5 |
| Lactic acid | 3.4 |
| Mannitol | 22.5 | wherein the solution further comprises a preservative and the pH of the solution is in the range of 3.9 to 4.5. Further, the sterile solution is contained in an injection device such as a pen injection device. In one preferred aspect, the preservative is phenol and it is present at a concentration of about 5 mg/ml.

In another preferred embodiment, the sterile solution of octreotide or its pharmaceutically acceptable salt comprises:

| Ingredients | Concentration in mg/ml |
|---|---|
| Octreotide base in the form of its salt | 2.0 |
| Lactic acid | 3.4 |
| Mannitol | 22.5 | wherein the solution further comprises a preservative and the pH of the solution is in the range of 3.9 to 4.5. Further, the sterile solution is contained in an injection device such as a pen injection device. In one preferred aspect, the preservative is phenol and it is present at a concentration of about 5 mg/ml.

In a specific embodiment, the present invention provides a sterile solution comprising: octreotide acetate present at a concentration equivalent to 2.5 mg/ml of octreotide base and at least one preservative in a pharmaceutically acceptable vehicle, wherein the sterile solution is present in an injection device in volume of 2.8 ml to 3.0 ml, and further wherein the injection device is configured to inject 20, 40, 60 and 80 microliters of the solution per injection to a patient in order to deliver octreotide in an amount of 50 μg, 100 μg, 150 μg and 200 μg per injection respectively. This sterile solution, when administered subcutaneously through the injection device to a human/patient, provides a bioavailability (i.e. $C_{max}$, $AUC_{0-t}$, $AUC_{0-\infty}$) that is equivalent to that obtained by administration of same dose of octreotide via subcutaneous injection of marketed 1 mg/ml octreotide solution (Sandostatin™), injected through a conventional needle syringe injection system. The sterile solution of these preferred embodiments further comprises phenol as the preservative present at a concentration in the range of 4 to 5 mg/ml and mannitol as an isotonicity agent present at a concentration ranging from 20 to 25 mg/ml, preferably at a concentration of 22.5 mg/ml. $C_{max}$, $AUC_{0-t}$, and $AUC_{0-\infty}$ observed upon subcutaneous administration of sterile solution of the present invention through the pen injection device were found to be within 85%-115% of that observed after subcutaneous administration of same dose of octreotide by injecting marketed 1 mg/ml octreotide solution (Sandostatin™) through conventional needle syringe injection system.

Alternatively, in other aspect, the present invention can be said to provide an injection device comprising a sterile solution of octreotide comprising octreotide in the form of a salt and present at a concentration equivalent to 2.0 mg/ml to 2.5 mg/ml of octreotide base and at least one preservative in a pharmaceutically acceptable vehicle.

In one embodiment, the present invention relates to an injection device containing multiple doses of octreotide in the form of a sterile solution of octreotide, the sterile solution comprising an octreotide salt, present at a concentration equivalent to 2.0 to 2.5 mg/ml of octreotide base and at least one preservative in a pharmaceutically acceptable vehicle, wherein the injection device is configured to inject 20 to 250 microliters of the solution per injection to provide multiple dosages of octreotide in an amount in the range from 40 μg to 625 μg per injection.

In one preferred embodiment, the present invention provides an injection device containing multiple doses of octreotide in the form of a sterile solution of octreotide acetate, the sterile solution comprising octreotide acetate present at a concentration equivalent to 2.0 to 2.5 mg/ml of octreotide base and at least one preservative in a pharmaceutically acceptable vehicle, wherein the injection device is suitable to inject 20 to 80 microliters of the solution per injection in order to provide multiple doses of octreotide in an amount in the range from 40 μg to 200 μg per injection.

In one particularly preferred embodiment, the present invention provides an injection device containing multiple doses of octreotide in the form of a sterile solution of octreotide acetate, the sterile solution comprising octreotide acetate present at a concentration equivalent to 2.5 mg/ml of octreotide base and at least one preservative in a pharmaceutically acceptable vehicle, wherein the injection device is configured to inject 20, 40, 60 or 80 microliters of the solution per injection in order to provide multiple doses of octreotide in an amount of 50 μg, 100 μg, 150 μg or 200 μg per injection respectively.

The injection device according to the present invention can be a single dose or a multiple dose injection device. This means that the reservoir or cartridge of the injection device either holds octreotide acetate solution in a volume equivalent to single dose or in volume equivalent to multiple doses. The injection device may have a reusable or disposable presentation. Preferably, the injection device is a device that is suitable for self-administration of the sterile solution medicament by the patient. The injection device according to the present invention may be selected from, but is not limited to a pen injection device, an auto-injector or a pre-filled syringe.

In preferred embodiments, the injection device is a pen injection device. The pen injection device comprises an upper body which is connected to a cartridge holder that holds a cartridge and a cap covering the cartridge holder. The tip of the cartridge holder has a threaded feature with provision of attaching a standard pen needle. The upper body is an assembly of components that allows selecting a particular dose and injecting the solution. The cartridge acts as a primary drug reservoir that contains octreotide acetate solution. Preferably, pen injection devices are multiple dose injection devices wherein the cartridge holds multiple doses of drug solution and the pen injection device is suitable for delivery of multiple injections or doses of drug until the cartridge is empty. The pen injection device is not limited by functionality and design and can have varied designs.

A pen injection device according to one embodiment of the present invention is preferably designed such that it is suitable for the subcutaneous application of the active substance which can be achieved by the provision of a hypodermic needle suitable for subcutaneous injection. A pen injection device according to one embodiment of the present invention preferably comprises a structural device e.g. a control dial or a dose dialing facility at the upper body region by means of which certain dosage of octreotide to be administered can be selected or adjusted (for example by selection of a certain administration volume in combination with known concentration of octreotide present in the solution) by the physician, the medical staff, or, in case of self-application by the patient. Thus, with this embodiment, the present invention also offers the possibility of selecting, if desired, intermediate dosages for which no other storage containers or injection devices, in particular no other injection bottles or ready-made syringes, are commercially available. In preferred embodiments the pen injection device has a dose dialing facility having a dose display with a pointer, dose set knob that allows the user to select a particular dose and dose button which when pressed, delivers the dose to the patient. In preferred most embodiments, the pen injection device have a dose selection knob with initial '0' μg unit setting and four dose settings that allow the user to select the desired unit dosage of 50, 100, 150, or 200 μg.

To deliver dose of octreotide, through the multiple dose pen injection device the user needs to attach a new needle on the tip of the cartridge holder, prime the pen prior to first use, select the dosage to be administered on the dose dial, insert the needle subcutaneously into the body of the patient at a predetermined injection location and inject the sterile solution by pushing the dose release button. If it is the first use, the user must prime the pen before use. The dosage dialing facility enables the priming of the multiple dose pen injection device prior to first use.

In some embodiments according to the present invention, the injection device is an auto-injector. Preferably, the auto-injector is designed to deliver a single dose of medicament, i.e. octreotide acetate. The auto-injector may comprise a pre-filled syringe or a cartridge as drug-reservoir and may have a disposable or reusable presentation. In one embodiment, the auto-injector comprises a pre-filled syringe with a disposable presentation. In another embodiment, the auto-injector has a replaceable cartridge and reusable presentation.

The auto-injector can have varied designs. An auto-injector according to one embodiment of the present invention is preferably designed such that it comprises following components: a central assembly or body portion that is suitable to hold a pre-filled syringe, the pre-filled syringe comprising a reservoir such as a barrel or a cartridge which stores the aqueous solution, the reservoir having a stalked needle at one end and a plunger stopper at other end. The central body portion may be made up of a plastic or polymeric material and may have a clear inspection window through which the solution in reservoir is visible. The auto-injector may further comprise a front assembly having a cap portion that holds a needle shield or tip cap, and it is attachable to the central assembly covering the stalked needle and sealing the needle tip opening. The auto-injector may further comprise a rear assembly which can have a spring assembly, plastic rod and an activation button. During self-administration of the aqueous solution, the cap along with needle shield should be removed from the body portion exposing the needle and subsequently after placing the body portion of the auto-injector at the site of administration the activation button should be pressed to push the plastic rod with spring assembly towards the plunger stopper. This will affect delivery of the aqueous solution through the needle to the patient.

The sterile solution according to the present invention comprises at least one preservative. Examples of the suitable preservatives that may be used include, but are not limited to, phenol, benzyl alcohol, m-cresol, methyl parabens, propylparaben, butylparaben, chlorbutanol, thimerosal, phenylmercuric salts, and the like or mixtures thereof.

The pharmaceutically acceptable vehicle according to the present invention comprises an aqueous vehicle, such as water for injection. It may further comprise one or more pH adjusting agents, buffering agents, isotonicity agents or chelating agents.

In one embodiment, the pH of the sterile solution is in the range of 3.9 to 4.5. The pH may be adjusted in the said range with the help of pH adjusting agents such as sodium bicarbonate, lactic acid, hydrochloric acid, acetic acid, sodium hydroxide and the like. A buffering agent or a buffer system may be used to maintain the pH in desired range. Suitable buffers that may be used include, but are not limited to lactate buffer, acetate buffer, citrate buffer, gluconate buffer, tartrate buffer, phosphate buffer and the like. In preferred embodiments, the sterile solution comprises lactic acid at a concentration of 3 to 4 mg/ml, preferably 3.4 mg/ml and sodium bicarbonate is used to adjust the pH in the range of 4.2±0.3.

In preferred embodiments, the osmolality of the sterile solution is in the range of 220 to 290 mOsm/Kg, preferably 230 to 280 mOsm/Kg. The osmolality may be adjusted in the said range with the help of an isotonicity agent. Typical isotonicity agents that may be used in the sterile solution include, but are not limited to mannitol, sorbitol, sodium chloride, potassium chloride, lactose, sucrose, maltose, trehalose, dextrose and mixtures thereof. In a preferred embodiment, mannitol is used as an isotonicity agent and it is preferably present in the sterile solution in an amount of 20.0-25.0 mg/ml of the solution. In a most preferred embodiment, the sterile solution comprises 22.5 mg/ml mannitol as an isotonicity agent. The sterile solution may optionally comprise a chelating agent such as disodium edetate, edetic acid, ethylene diamine tetraacetic acid and the like.

In one preferred embodiment, phenol is used as a preservative in an amount ranging from about 2.0 mg/ml to 6.0 mg/ml of the solution, preferably from about 4.0 to 5.0 mg/ml of the solution. In one specific embodiment, the solution comprises octreotide in the form of its salt at a concentration of 2.5 mg of octreotide per ml of the solution and about 4.0 to 5.0 mg per ml of phenol as preservative. In another embodiment, the preservative that may be used is benzyl alcohol and is present in an amount of about 7.0 mg/ml to 12.0 mg/ml of the solution. In one specific embodiment, the solution comprises octreotide in the form of a salt at a concentration of 2.5 mg of octreotide per ml of the solution and about 9.0-11.25 mg per milliliter of benzyl alcohol. In another embodiment, the preservative is m-cresol and is present in an amount ranging from about 1.5 mg/ml to 9.0 mg/ml of the solution, preferably from about 2.0 to 4.0 mg/ml of the solution. In another embodiment, the preservative is methyl paraben and is present in an amount of about 0.1 mg/ml to 4.0 mg/ml, preferably in an amount of 0.65 mg/ml to 2.5 mg/ml of the solution. In another embodiment, the preservative is propyl paraben and is present in an amount of about 0.05 mg/ml to 2.0 mg/ml of the solution, preferably in an amount of 0.2 mg/ml. In another embodiment, the preservative is butyl paraben and is present in an amount of about 0.06 mg/ml to 1.0 mg/ml of the solution. In another embodiment, the preservative is chlorobutanol and is present in an amount of about 0.5 mg/ml to 10 mg/ml, preferably in an amount of 2.0 to 8.0 mg/ml of the solution. In another embodiment, the preservative is thiomersal and is present in an amount of about 0.01 mg/ml to 1.5 mg/ml of the solution, preferably in an amount of 0.05 to 0.5 mg/ml of the solution. The sterile aqueous solution of octreotide contained in the injection device such as a pen injection device remains sterile during in-use and during the shelf life.

The sterile solution of octreotide or its pharmaceutically acceptable salt thereof contained in the injection device and according to the present invention comprises: a higher concentration of octreotide base (2.0 to 2.5 mg/ml) as compared to that of marketed product, which is a prior known dilute solution (1.0 mg/ml octreotide). For instance, for administration of a particular dosage, a lower volume of the sterile solution is required to be injected in comparison to the volume of prior known dilute solutions. This in-turn provides one advantage of the invention, in that a considerably reduced amount of preservative is injected per dose (per day) in the body as compared to prior art known octreotide products like Sandostatin™. For instance, the prior art known octreotide acetate solution of Sandostatin™ having 1.0 mg/ml octreotide contains X mg/ml of a preservative. The solution according to the present invention has octreotide in the range of from 2.0 to 2.5 mg/ml and X mg/ml of preservative for maintaining sterility. So, when a particular dose of octreotide is administered using the injection device according to the present invention, the volume of solution to be injected is 2.0 to 2.5 times lower as compared to the prior art known dilute solutions and therefore the amount of preservative injected is X/2.0 to X/2.5. This is illustrated in Table below:

subcutaneous injection of a 100 µl marketed solution having 1 mg/ml octreotide. In another aspect, the injection device contains multiple doses of octreotide in the form of its sterile solution, the sterile solution comprising octreotide acetate at a concentration equivalent to 2.0 mg/ml octreotide base and a preservative, wherein when the injection device delivers 100 µg of octreotide in a 50 µl injection volume, the amount of preservative delivered is 2.0 times less than that delivered by subcutaneous injection of a solution that contain 1 mg/ml octreotide and 100 µl of the solution is injected.

| | | | Volume of solution injected per day (µL) | | Amount of preservative injected per day (µg) | |
|---|---|---|---|---|---|---|
| Indication | Prescribed Dose | Illustrative Daily dose injected (µg) | Sterile solution of Example 1 of the present invention delivered by Pen Injection device | Prior known Sandostatin ™ product delivered by conventional syringe (octreotide 1 mg/ml and preservative 5 mg/ml) | Sterile solution of Example 1 of the present invention delivered by PenInjection device | Prior known Sandostatin ™ product delivered by conventional syringe (octreotide 1 mg/ml and preservative 5 mg/ml) |
| Acromegaly | Dose most commonly effective is 100 µg t.i.d. but some patients may require 500 µg t.i.d | 300 | 120 | 300 | 600 | 1500 |
| Carcinoid Tumors - Initial Therapy 1st two week | Median daily maintenance dose is approximately 450 µg | 450 | 180 | 450 | 900 | 2250 |
| VIPomas - Initial Therapy 1st two week | Daily dosages of 200-300 µg are recommended during initial therapy | 200 | 80 | 200 | 400 | 1000 |

According to one embodiment, the sterile solution comprises octreotide in the form of its salt present at a concentration equivalent to 2.5 mg/ml of octreotide base in a pen injection device, wherein when the injection device delivers 100 µg of octreotide in a 40 µl injection volume, the amount of preservative delivered is 2.5 times less than that delivered by subcutaneous injection of 100 µl of a solution having 1 mg/ml of octreotide base.

According to another embodiment, the sterile solution comprises octreotide in the form of its salt at a concentration equivalent to 2.5 mg/ml of octreotide base in a pen injection device, wherein when the injection device delivers 200 µg of octreotide in an 80 µl injection volume, the amount of preservative delivered is 2.5 times less than that delivered by subcutaneous injection of 200 µl of the solution having 1 mg/ml of octreotide base.

According to another embodiment, the sterile solution comprises octreotide in the form of its salt at a concentration equivalent to 2.0 mg/ml of octreotide base in an injection device, wherein when the injection device delivers 100 µg of octreotide in a 50 µl injection volume, the amount of preservative delivered is 2.0 times less than that delivered by subcutaneous injection of 100 µl of the solution having octreotide in the form of its salt at a concentration equivalent to 1 mg/ml of octreotide base.

In one aspect, the injection device contains multiple doses of octreotide in the form of its sterile solution, the sterile solution comprising octreotide acetate at a concentration equivalent to 2.5 mg/ml of octreotide base and a preservative, wherein to deliver 100 µg of octreotide, a 40 µl solution is injected subcutaneously through the pen injection device and the amount of preservative delivered is 2.5 times less than the amount of preservative that is delivered upon In one aspect, the present invention relates to a method for the treatment of diseases selected from acromegaly, carcinoid tumour, vasoactive intestinal peptide tumour and combinations thereof, in a patient in need thereof, comprising the steps of: subcutaneously administering to said patient a sterile solution comprising octreotide acetate present at a concentration equivalent to 2.0 to 2.5 mg/ml of octreotide base and at least one preservative in a pharmaceutically acceptable vehicle. The sterile solution is contained in an injection device such as a pen injection device that is configured to subcutaneously inject 20 to 250 microliters of the solution per injection in order to provide multiple doses of octreotide in an amount in the range from 40 µg to 625 µg per injection. The solution is present in the injection device in volumes ranging from 2.0 ml to 5.0 ml. In preferred embodiment, the solution further comprises mannitol in an amount ranging from about 20 mg/ml to about 25 mg/ml and the pH of the solution is in the range of 3.9 to 4.5.

In the context of this specification "comprising" is to be interpreted as "including". Aspects of the invention comprising certain elements are also intended to extend to alternative embodiments "consisting" or "consisting essentially" of the relevant elements. Where technically appropriate, embodiments of the invention may be combined.

Embodiments are described herein as comprising certain features/elements. The disclosure also extends to separate embodiments consisting or consisting essentially of said features/elements.

Hereinafter, the invention is more specifically described by way of examples. The examples are not intended to limit the scope of the invention and are merely used as illustrations.

Example 1

Sterile solution of octreotide acetate according to one embodiment of the present invention is described below.

TABLE 1

Sterile solution of the present invention

| Sr. No. | Ingredients | mg/ml |
|---|---|---|
| 1 | Octreotide acetate equivalent to octreotide base | 2.5 |

Finally, a specified volume (2.8 ml) of solution so formed was filled aseptically in pre-sterilized cartridge of a pen injection device and the cartridge was then sealed.

Storage Stability Testing—

The sterile solution of example 1 contained in the glass cartridge of multiple dose pen injection device, was then subjected to stability studies at 2-8° C. for a period of 24 months and at 25° C./60% Relative Humidity (accelerated conditions) for a period of 6 months. In this storage period, the device was not used i.e. no solution was withdrawn and the cartridge was not punctured. It was analyzed for the assay and related substances. The assay of phenol was also determined. The results are tabulated in the Table 2 below.

TABLE 2

Result of stability study of octreotide acetate injection, 2.5 mg/ml

| Stage | Assay of Octreotide | Related Substances | | | | | | Total Imp | pH | Assay of Phenol | Transmittance at 650 nm |
|---|---|---|---|---|---|---|---|---|---|---|---|
| | | Imp C | Imp D | Imp E | Imp F | Imp G | Highest Unknown. Impurity | | | | |
| Limits (US) | 90.0-110.0% of L.C.* | NMT 0.5% | NMT 1.0% | NMT 1.0% | NMT 1.0% | NMT 1.0% | NMT 0.5% | NMT 4.0% | 3.9-4.5 | 80.0-120.0% of L.C.* | NLT 95.0% |
| Initial | 106.9 | 0.082 | ND | ND | 0.271 | 0.135 | 0.165 | 1.712 | 4.18 | 99.4 | 99.97 |
| Stage: 25° C./60% RH (Accelerated study); Orientation: On the side | | | | | | | | | | | |
| 3 Month | 104.6 | 0.066 | ND | ND | 0.276 | 0.143 | 0.367 | 2.206 | 4.12 | 100.8 | 97.20 |
| 6 Month | 105.6 | 0.019 | 0.007 | ND | 0.288 | 0.141 | 0.369 | 1.868 | 3.96 | 100.0 | 98.88 |
| Stage: 2-8° C. (Long term study); Orientation: On the side | | | | | | | | | | | |
| 3 Month | 103.9 | 0.076 | ND | ND | 0.265 | 0.135 | 0.174 | 1.776 | 4.19 | 101.0 | 99.90 |
| 6 Month | 106.83 | 0.019 | 0.006 | ND | 0.289 | 0.140 | 0.155 | 1.544 | 4.02 | 100.54 | 100.00 |
| 12 Month | 103.09 | 0.073 | ND | 0.008 | 0.266 | 0.142 | 0.241 | 1.556 | 4.03 | 99.9 | 99.90 |
| 24 Month | 105.69 | 0.06 | 0.018 | 0.009 | 0.261 | 0.141 | 0.208 | 1.519 | 4.01 | 100.81 | 99.41 |

L.C.*—Label claim
NMT—Not More Than
NLT—Not Less Than
ND—Not Detected

TABLE 1-continued

Sterile solution of the present invention

| Sr. No. | Ingredients | mg/ml |
|---|---|---|
| 2 | Lactic acid | 3.4 |
| 3 | Mannitol | 22.5 |
| 4 | Phenol | 5.0 |
| 5 | Sodium bicarbonate | q.s. to pH 4.2 ± 0.3 |
| 6 | Water for injection | q.s to 1 ml |

Procedure: Specified volume of water for injection was collected in suitable container at a temperature of 20° C. to 25° C. To this octreotide acetate was added under stirring to form a clear solution. Specified quantity of lactic acid was dissolved in above solution under stirring until the clear solution was obtained. Specified quantity of mannitol was dissolved in the above solution under stirring until the clear solution was obtained. Separately phenol was dissolved in the specified quantity of water and added to the above bulk solution. Further, the pH of the solution was adjusted to about 4.20±0.30 with sufficient quantity of sodium bicarbonate solution. This unfiltered bulk solution was stored under nitrogen blanket until before subjecting to membrane filtration. The bulk solution of octreotide acetate was sterilized by aseptic filtration through a set of 0.45 micron Nylon 66 capsule filter and 0.2 micron Nylon 66 capsule filter and filtered solution was stored under nitrogen blanket.

The results of the aforesaid stability tests indicated that the solution stored in the multiple dose pen injection device when kept at 2-8° C. for a period of 24 months or at 25° C./60% Relative Humidity for a period of 6 months, remains stable, wherein the assay of octreotide acetate remains within the limit of 95-110% of label claim, and the assay of phenol preservative remains within the limit of 80-120% of label claim, and the related substance/impurities remained within desired limits. This indicate that the sterile solution of the present invention in the multiple dose pen injection device remains stable on storage throughout the shelf life of the product.

Example 2

The aqueous solution of octreotide acetate having concentration equivalent to 2.5 mg/ml of octreotide base filled in a pen injection device according to example 1 of the present invention, referred to herein as test product A, was subjected to in-vivo plasma pharmacokinetic study in healthy human volunteers, whereby a given dose of octreotide acetate solution (equivalent to 100 µg octreotide base) was delivered sub-cutaneously through the multiple dose pen injection device to the human volunteer and plasma pharmacokinetic profile of octreotide was studied. The bioavailability i.e. $AUC_{0-\infty}$, $AUC_{0-t}$, $C_{max}$, $T_{max}$, and other pharmacokinetic parameters were determined. The study was a randomized, open label, two treatment, two period, two sequence, single dose, cross-over study, under fasting conditions and involving twelve healthy adult human volunteers, with a washout period of 7 days between dosages. The marketed product Sandostatin™ 1.0 mg/ml solution in multi-dose vial was taken as control (C), wherein same dose, i.e. equivalent to 100 µg octreotide base was delivered to healthy human volunteers using conventional syringe after withdrawal from the vial.

Before dosing, the volunteers were kept on an overnight fasting for 10 hours. The test product A, i.e. octreotide acetate 2.5 mg/ml solution, was administered subcutaneously through the pen injection device following priming the pen and dose dialing to deliver 40 µL of sterile octreotide acetate 2.5 mg/ml solution corresponding to a 100 µg dosage. The control (C), i.e. octreotide acetate 1.0 mg/ml Sandostatin™ solution was administered by first carefully withdrawing 100 µL solution from the product vial (corresponding to a 100 µg dose) using a syringe followed by subcutaneous injection of the solution by the study physician to the healthy adult volunteers.

In each of the two study periods, 19 blood samples were collected including pre-dose blood sample. A pre-dose blood sample of 5 ml was collected within 1 hour prior to schedule dosing. Post-dose blood samples (5 ml each) were collected at 0.083, 0.167, 0.250, 0.333, 0.500, 0.667, 0.833, 1.000, 1.250, 1.500, 2.000, 3.000, 4.000, 5.000, 6.000, 7.000, 8.000 and 10.000 hours. The concentration of octreotide in plasma was quantitated using a validated LC/MS/MS method. The mean plasma octreotide concentration (pg/ml)–time profile after administration of test product and reference product were plotted and is presented in FIG. 1. The pharmacokinetic parameters viz. $C_{max}$, $T_{max}$, $AUC_{0-t}$, $AUC_{0-\infty}$, $t_{1/2}$ were determined and the geometric mean values for the test product (A) and control (C) are presented below in Table 3.

TABLE 3

Pharmacokinetic parameters for the test product (A) and Control (C).

| Geometric Mean Pharmacokinetic parameters | Test Product (A) (example 1) | Control (C) (Sandostatin ™) | % A/C |
|---|---|---|---|
| $C_{max}$ (pg/ml) | 5279.01 | 5286.13 | 99.865 |
| $AUC_{0-t}$ (pg * hr/ml) | 15778.13 | 17493.27 | 90.195 |
| $AUC_{0-\infty}$ (pg * hr/ml) | 16642.57 | 18676.57 | 89.109 |
| $T_{max}$ (hour) | 0.44 | 0.48 | — |
| $t_{1/2}$ (hour) | 2.45 | 2.52 | — |

The mean values of $C_{max}$, $AUC_{0-t}$, $AUC_{0-\infty}$ for the test product (A) were found to be equivalent to that of Control (C) and were within the range of 85%-115% of the Control (C).

Figure 1:
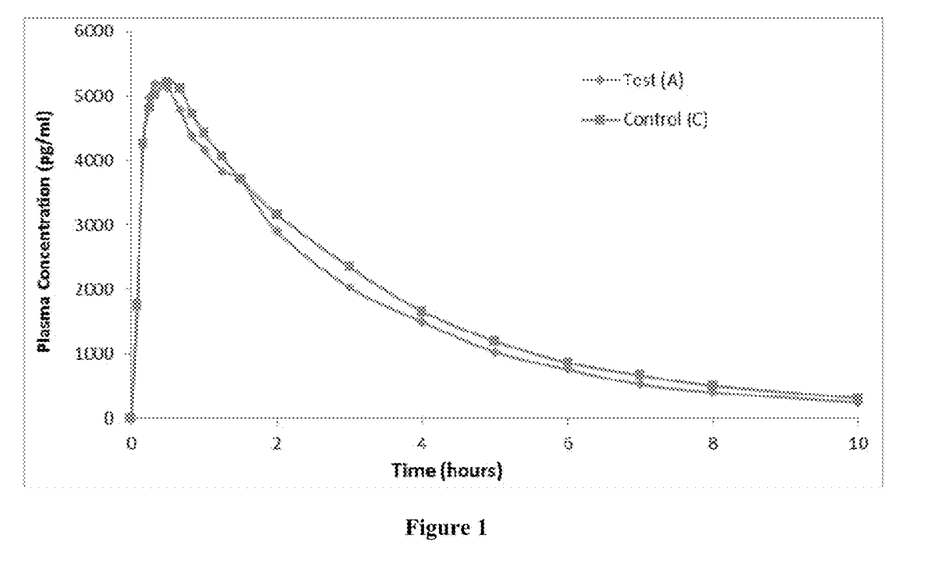
FIG. 1 represents a plot of mean plasma octreotide concentration (pg/ml) versus time (hour) profile for test product (A) and control (C), according to example 2.

It is evident from FIG. 1 and Table 3 that the bioavailability of octreotide obtained upon subcutaneous administration of aqueous solution of example 1 (test product A) was equivalent to that obtained upon subcutaneous administration of Sandostatin™ 1.0 mg/ml (control C).

Comparative Example-I

Table 4 summarizes a sterile solution of octreotide acetate having a concentration equivalent to 5.0 mg/ml of octreotide base.

| | Ingredients | Concentration in mg/ml |
|---|---|---|
| 1 | Octreotide acetate equivalent to octreotide base | 5.0 |
| 2 | lactic acid | 3.4 |
| 3 | mannitol | 45.0 |
| 4 | phenol | 5.0 |
| 5 | sodium bicarbonate | q.s. to pH 4.2 ± 0.3 |
| 6 | Water for injection | q.s to 1 ml |

The solution was prepared by following a procedure similar to example 1.

The aqueous solution of octreotide acetate having a concentration equivalent to 5 mg/ml of octreotide base in a pen injection device as per comparative example I, referred to herein as test product B, was subjected to in-vivo plasma pharmacokinetic study in healthy human volunteers, whereby a given dose of octreotide acetate solution (equivalent to 100 µg octreotide base) was delivered subcutaneously through the multiple dose pen injection device and the pharmacokinetic parameters so observed were compared with that of control solution, i.e. marketed Sandostatin™ 1.0 mg/ml octreotide solution. A randomized, open label, two treatment, two period, two sequence, single dose (100 µg octreotide acetate), cross-over study, under fasting conditions was performed in twelve health adult volunteers at a dose of 100 µg. All of them completed the two way cross-over study. The washout period was 6 days between dosages.

The solution of octreotide acetate having a concentration equivalent to 5 mg/ml of octreotide base as per comparative example I, was delivered to healthy human volunteers using the pen injection device in a manner similar to that described in Example 2, and the plasma pharmacokinetic profile was studied and the bioavailability i.e. $AUC_{0-\infty}$, $C_{max}$ and other pharmacokinetic parameters were determined. The marketed product Sandostatin™ 1.0 mg/ml solution in multi-dose vial was taken as control (C), wherein the dose was delivered to healthy human volunteers using conventional syringe after withdrawal from the vial.

Before dosing, the volunteers were kept on an overnight fasting for 10 hours. The test product B, was administered subcutaneously through the pen injection device following priming and dose dialing. For delivery of a 100 µg dosage, the pen injection device was dialed to deliver 20 µL of sterile octreotide acetate 5.0 mg/ml solution followed by subcutaneously injection of the solution through the pen injection device.

The control (C), i.e. octreotide acetate 1.0 mg/ml solution was administered by first carefully withdrawing 100 µL solution from the product vial which was corresponding to a 100 µg dosage using a syringe followed by subcutaneous injection of the solution by the study physician to the healthy adult volunteers.

Figure 2:
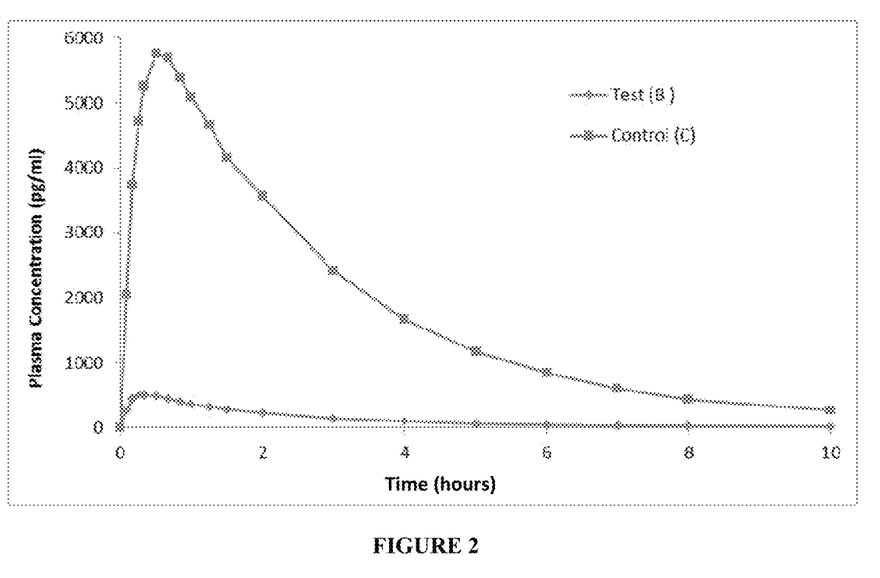
FIG. 2 represents a plot of mean plasma octreotide concentration (pg/ml) versus time (hour) profile for test product (B) and control (C), according to comparative example I.

The sampling schedule was similar to that of Example 2. The concentration of octreotide in plasma was quantitated using a validated LC/MS/MS method. The mean plasma octreotide concentration (pg/ml)–time profile after administration of test product and reference product were plotted and compared (FIG. 2). The pharmacokinetic parameters viz. $C_{max}$, $T_{max}$, $AUC_{0-t}$, $AUC_{0-\infty}$, $t_{1/2}$ were determined and the geometric mean values for the test product (B) and control (C) are presented below in Table 5.

TABLE 5

Pharmacokinetic parameters for the test product (B) and Control (C).

| Geometric Mean Pharmacokinetic parameters | Test Product (B) (comparative example I) | Control (C) (Sandostatin ™) | % B/C |
|---|---|---|---|
| $C_{max}$ (pg/ml) | 404.35 | 5893.36 | 6.861 |
| $AUC_{0-t}$ (pg * hr/ml) | 877.48 | 18095.46 | 4.849 |
| $AUC_{0-\infty}$ (pg * hr/ml) | 1010.32 | 18966.60 | 5.327 |
| $T_{max}$ (hour) | 0.39 | 0.65 | — |
| $t_{1/2}$ (hour) | 2.27 | 2.33 | — |

The mean values of $C_{max}$, $AUC_{0-t}$, $AUC_{0-\infty}$, for the test product (B) were substantially lower than the Control (C).

It is apparent from FIG. 2 and Table 5 that the bioavailability of octreotide observed upon sub-cutaneous administration of aqueous solution of octreotide having concentration of 5.0 mg/ml (as per comparative example 1) was only about 5% as compared to that of control, Sandostatin™ 1 mg/ml injection and was therefore not-bioequivalent.

Surprisingly, the blood levels of octreotide, i.e. $C_{max}$, $AUC_{0-t}$, $AUC_{0-\infty}$, upon subcutaneous administration of same dosage of octreotide by injecting aqueous solution of octreotide of example 1 (that have lower concentration of 2.5 mg/ml) was found to be higher, (FIG. 1, Table 3) and comparable to that of the control—Sandostatin™ 1.0 mg/ml injection.

The invention claimed is:

1. A sterile solution comprising: octreotide in the form of a pharmaceutically acceptable salt, present at a concentration equivalent to 2.5 mg/ml of octreotide base, mannitol in an amount ranging from about 20 mg/ml to about 25 mg/ml and at least one preservative in a pharmaceutically acceptable vehicle, wherein the sterile solution is present in an injection device.

2. The sterile solution according to claim 1, wherein the volume of solution contained in the injection device is in the range of 2.8 ml to 3 ml.

3. The sterile solution according to claim 1, wherein the preservative is selected from the group consisting of phenol, benzyl alcohol, m-cresol, methyl parabens, propylparabens, butylparabens, chlorbutanol, thimerosal, phenylmercuric salts and mixtures thereof.

4. The sterile solution according to claim 1, wherein the solution comprises mannitol in an amount of about 22.5 ng/ml.

5. The sterile solution according to claim 1, comprising:

| Ingredients | Concentration in mg/ml |
|---|---|
| octreotide base in the form of its salt | 2.5 |
| lactic acid | 3.4 |
| mannitol | 22.5 | wherein the pH of the sterile solution is in the range from 3.9 to 4.5.

6. The sterile solution according to claim 1, wherein the injection device is configured to inject 20 µl to 250 µl of the sterile solution per injection.

7. The sterile solution according to claim 6, wherein the injection device is configured to inject 20 µl to 80 µl of the sterile solution per injection.

8. The sterile solution according to claim 1, wherein the injection device is a pen injection device.

* * * * *